United States Patent [19]

Lescrenier

[11] 4,442,533

[45] Apr. 10, 1984

[54] IMAGE PLANE INDICATOR

[76] Inventor: Charles Lescrenier, 660 Crescent Ct., Wauwatosa, Wis. 53213

[21] Appl. No.: 294,706

[22] Filed: Aug. 20, 1981

[51] Int. Cl.³ .............................................. G03B 41/16
[52] U.S. Cl. ...................................... 378/21; 378/25; 378/20 G
[58] Field of Search ................... 378/20 G, 21, 25, 26, 378/27

[56] References Cited

U.S. PATENT DOCUMENTS 4,117,337 9/1978 Saats ...................................... 378/20
4,315,156 2/1982 Sell ......................................... 378/26

Primary Examiner—Craig E. Church
Attorney, Agent, or Firm—Andrus, Sceales, Starke & Sawall

[57] ABSTRACT

An indicator for visibly defining the image plane located at the movable fulcrum of a tomography X-ray machine. The indicator includes a laser beam light source mounted for vertical movement along a rack and pinion assembly. As the fulcrum of the X-ray machine is raised or lowered with respect to the patient to take X-ray images along different horizontal planes, a pulse generator generates a signal responsive to the movement. The signal operates a servo-drive mechanism that moves the light source a corresponding vertical distance along the rack and pinion assembly.

6 Claims, 3 Drawing Figures

IMAGE PLANE INDICATOR

BACKGROUND OF THE INVENTION

FIELD OF THE INVENTION

The present invention is directed to a device for indicating the adjustable X-ray image plane of a moving fulcrum X-ray machine.

BACKGROUND OF THE INVENTION

DESCRIPTION OF THE PRIOR ART

In tomographic radiological diagnosis, the X-ray source and the film plate are mounted on opposite ends of a lever. The source and the film are coordinately moved in opposite linear directions in order to define an image plane within the patient's body at the fulcrum of the movement. As the source and film are so moved the film images of tissue not in the image plane become blurred by the movement while the images of tissue in the image plane remain clear and precise.

To take a series of X-rays through a plurality of planes, the table and patient are typically moved up and down with respect to the apparatus or the X-ray equipment is moved up and down with respect to a fixed table.

It is known to indicate the X-ray image plane by means of a beam of light projected on the side of the patient. However, it is desirable to have this visual indicator automatically adjust to the movement of the imaging plane as a series of X-rays are taken through different planes in the patient.

If the position of the image plane is varied by vertically moving the table, the image plane indicator may be mounted at a fixed position opposite the stationary fulcrum of the X-ray equipment to simply and easily show the imaging plane.

However, if the X-ray source, film plate and associated fulcrum are moved for varying the position of the image plane, it become more difficult to visually define the image plane, since it is necessary to provide an image plane indicator that follows the moving fulcrum.

SUMMARY OF THE PRESENT INVENTION

The present invention is thus directed to an image plane indicator for use with moving fulcrum tomographic X-ray equipment.

More particularly the present invention is directed to such an indicator providing a visual indication of the X-ray image plane that automatically responds to and adjusts itself for the movement of the fulcrum of the lever containing the X-ray source and film as a series of X-rays are taken through differing horizontal planes.

For this purpose, the present invention includes a movable light beam source that applies a beam of light to the patient along the X-ray image plane. A pulse generator generates electrical signals in response to the movement of the fulcrum. A servo-drive mechanism is connected to the pulse generator. The electrical signal produced by the movement of the fulcrum activates the servo-drive which in turn moves the light beam source a corresponding distance by means of a rack and pinion arrangement. The visual indication of the image plane of the X-ray device thus automatically adjusts to the movement of the tomographic fulcrum.

BRIEF DESCRIPTION OF THE DRAWINGS

The drawings illustrate the best mode presently contemplated of carrying out the invention.

In the drawings

DETAILED DESCRIPTION OF THE PREFERRED EMBODIMENT

Figure 1:
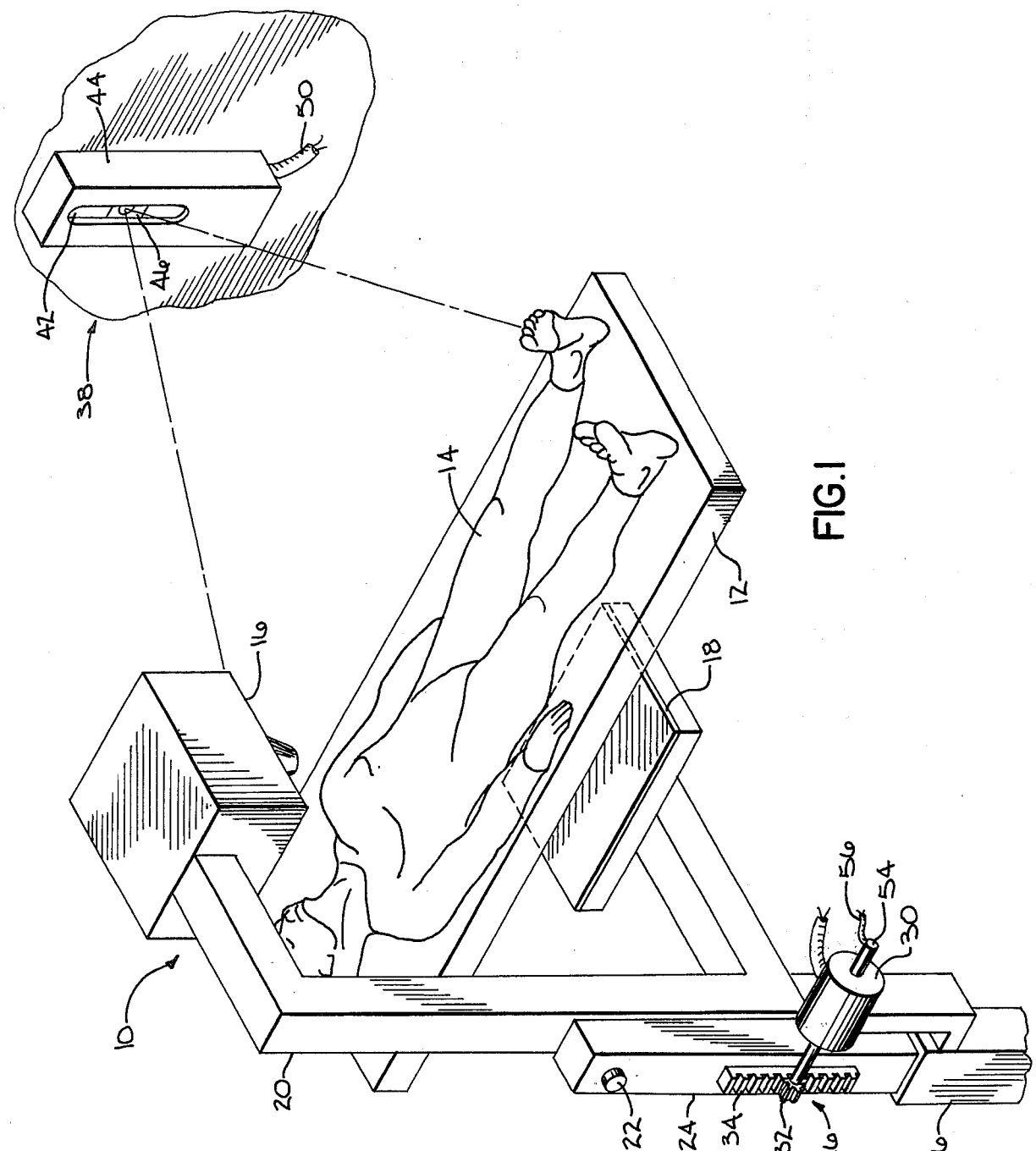
FIG. 1 is a perspective view of a moving fulcrum tomographic machine utilizing the image plane indicator of the present invention.
Figure 4:
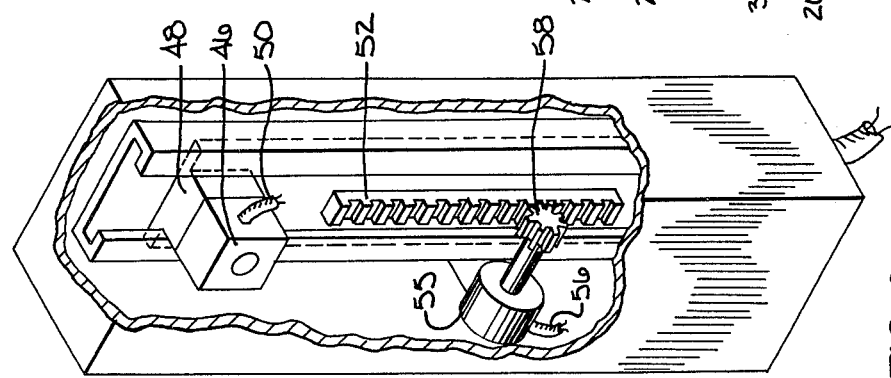
FIG. 4 is a perspective view with parts broken away of the image plane indicator of the present invention.

As seen in FIG. 1 the conventional moving fulcrum tomographic system 10 includes a table 12 for supporting the patient 14 beneath an X-ray source 16.

X-ray source 16 and X-ray film 18 are mounted on a C-shaped lever 20 that is mounted for rotational movement about fulcrum 22 and for vertical movement on beam 24 containing rack and pinion assembly 26.

Figure 2:
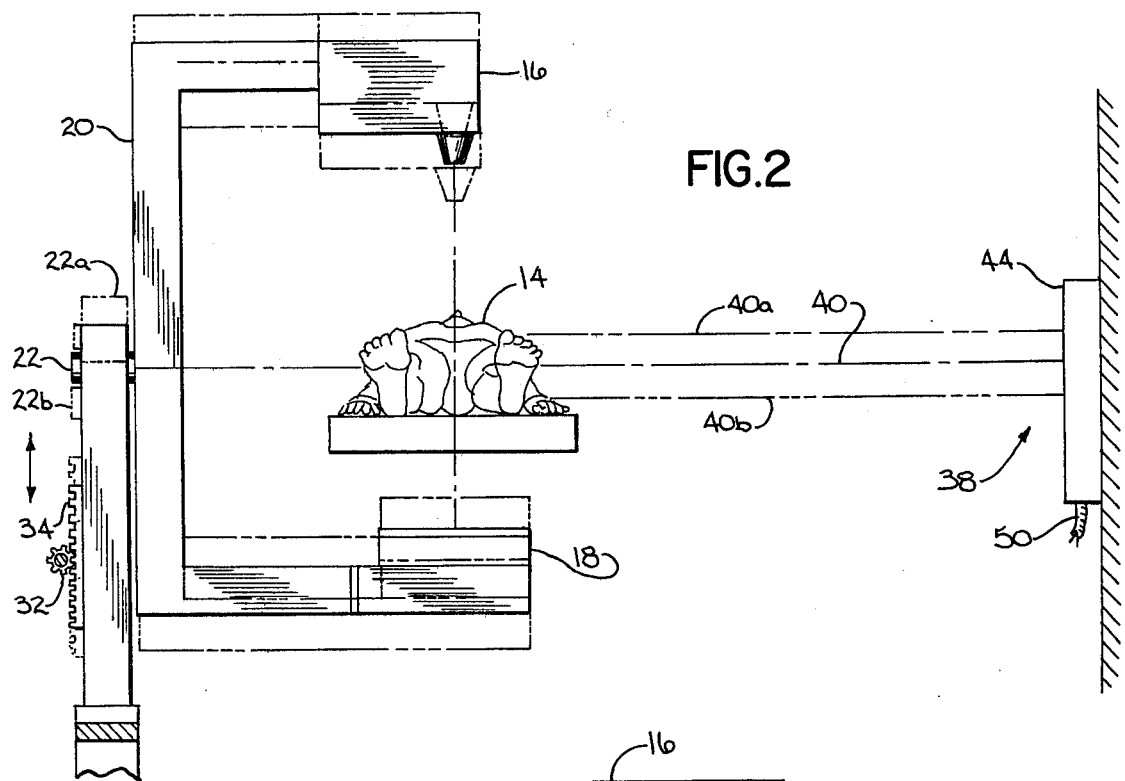
FIG. 2 is a front view of the moving fulcrum tomographic machine of FIG. 1 with the upward and downward movement of the machine shown in phantom.
Figure 3:
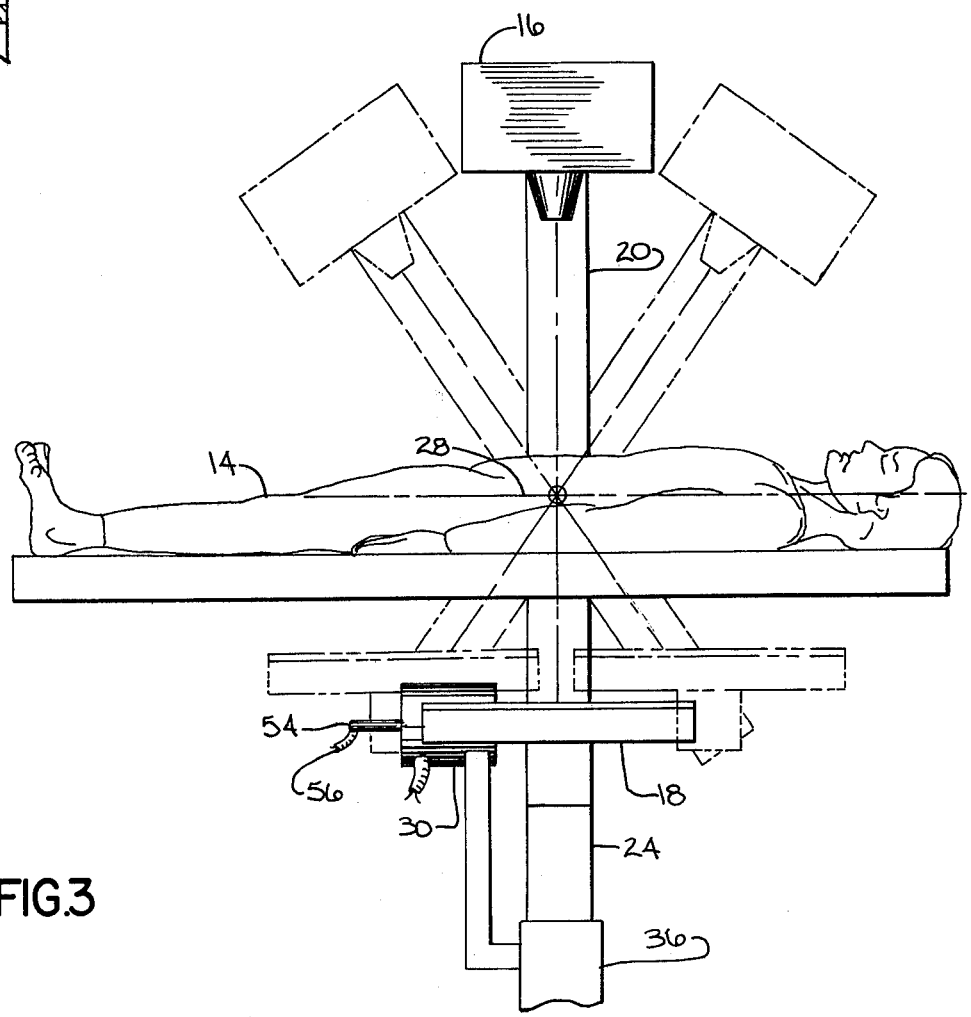
FIG. 3 is a side view of the moving fulcrum tomographic machine of FIG. 1 with the rotational movement of the machine shown in phantom.

The rotational movement of lever 20 (phantom lines of FIG. 3) allows for the taking of an X-ray along a precise image plane within patient 14 identified as 28 in FIG. 3 located at fulcrum 22 of the system. The vertical movement of fulcrum 22 and the other portions of the X-ray system (phantom lines of FIG. 2) permits a series of X-rays to be taken along a plurality of parallel image planes.

The vertical movement of lever 20 is controlled by a motor 30 that rotates pinion 32 and causes rack 34 mounted on beam 24 to move vertically thus moving beam 24 vertically and telescopically with respect to support 36.

Mounted on the wall opposite fulcrum 22 is image plane indicator 38. Image plane indicator 38 furnishes a visual indication, in the form of a projected laser beam 40, of the X-ray image plane on the side of patient 14. The technician is thus provided with a visual indication of the location of the image plane.

Laser beam 40 is projected through aperture 42 in casing 44 and onto patient 14 by means of lens assembly 46 mounted on slide 48. The laser light itself is generated by a laser (not shown) remote from indicator 38 and the light is then transmitted to lens assembly 46 by means of fiber optic cable 50.

Slide 48 is mounted for vertical movement within casing 44 and includes rack 52 mounted on its inner surface.

The movement of lever 20 and fulcrum 22 is monitored by a photo electric or magnetic type pulse generator 54 connected to servo-drive 55, by conductor 56. Vertical movement of lever 20 will result in the generation of an electrical signal that is transmitted to servo-drive 55. Servo-drive 55 then rotates pinion 58 causing rack 52 to move vertically.

Indicator 38 is initially calibrated in such a manner that beam 40 is projected onto fulcrum 22, thus providing proper image plane indication.

Any vertical movement by lever 20 is matched by an identical corresponding vertical movement of slide 48 thereby to maintain the image plane indication. Thus, as fulcrum 22 moves up or down to positions 22a and 22b in order to take X-rays in other planes projected laser beam 40 will move vertically to positions 40a and 40b so that an accurate visual indication of the image plane is projected onto the side of patient 14 at all times.

Various modes of carrying out the invention are contemplated as being within the scope of the following claims particularly pointing out and distinctly claiming the subject matter which is regarded as the invention.

I claim:

1. In an X-ray device in which the X-ray generator and image receptor are movable about a fulcrum that defines the plane of the image appearing on the receptor, the fulcrum being movable relative to an object being imaged and normal to the image plane to establish the location of the image plane in the object, an image plane indicator comprising:

indicating means movable with respect to the object normal to the plane of the image for providing a visually perceptible indication on the object of the image plane location;

detection means operably connected to the movable fulcrum, said detection means generating a signal responsive to movement of the fulcrum; and positioning means operably connected to said detection means and to said indicating means, said positioning means moving said indicating means in response to said signal generated by said detection means for maintaining the visually perceptible indication at the image plane location as the fulcrum is moved.

2. The image plane indicator defined in claim 1 wherein said detection means comprises a pulse generator operatively connected to the fulcrum for generating a pulse signal responsive to movement of the fulcrum, and wherein said positioning means is responsive to the pulse signal for moving said indicating means.

3. The image plane indicator as defined in claim 1 wherein said positioning means comprises a servo-drive mechanism connected to a rack and pinion assembly mounted on said indicating means, said servo-drive mechanism being responsive to said signal generated by said detection means for moving said indicating means as the fulcrum is moved so as to maintain the visually perceptible indication at the image plane location as the fulcrum is moved.

4. The image plane indicator defined in claim 1 wherein said indicating means includes means providing a visible laser beam and wherein said indicating means is mounted on said positioning means.

5. The image plane indicator defined in claim 4 wherein said laser beam is generated at a point remote from said indicating means and said laser beam is conveyed to said indicating means through fiber optic means.

6. In an X-ray device in which the X-ray generator and image receptor are movable about a fulcrum that defines the plane of the image appearing on the receptor, the fulcrum being movable relative to a patient being imaged and normal to the image plane to establish the location of the image plane in the patient, an image plane indicator comprising:

means providing at least one visible laser beam for projection on the patient to provide an indication of the location of the image plane in the patient;

a pulse generator operatively connected to the fulcrum for generating an electrical signal responsive to movement of the fulcrum with respect to the patient;

a servo-drive mechanism operatively connected to said pulse generator and powered by said electrical signal; and a rack and pinion assembly connected to said servo-drive mechanism for moving said rack with respect to said pinion in correspondence with the movement of the fulcrum, said laser beam means being mounted on said rack and pinion assembly for movement normal to the plane of the image as the fulcrum is moved so as to maintain the beam at the location of the image plane as the fulcrum is moved.

* * * * *